US012690929B2

(12) United States Patent
Stopp et al.

(10) Patent No.: US 12,690,929 B2
(45) Date of Patent: Jul. 28, 2026

(54) COMPENSATION OF GRAVITY-RELATED DISPLACEMENTS OF MEDICAL CARRIER STRUCTURES

(71) Applicant: Brainlab SE, Munich (DE)

(72) Inventors: Sebastian Stopp, Munich (DE); Nils Frielinghaus, Heimstetten (DE)

(73) Assignee: Brainlab SE, Munich (DE)

( * ) Notice: Subject to any disclaimer, the term of this patent is extended or adjusted under 35 U.S.C. 154(b) by 652 days.

(21) Appl. No.: 17/279,895

(22) PCT Filed: Jun. 18, 2020

(86) PCT No.: PCT/EP2020/066861
§ 371 (c)(1),
(2) Date: Mar. 25, 2021

(87) PCT Pub. No.: WO2021/254613
PCT Pub. Date: Dec. 23, 2021

(65) Prior Publication Data
US 2022/0183778 A1     Jun. 16, 2022

(51) Int. Cl.
*A61B 34/32*          (2016.01)
*A61B 34/00*          (2016.01)
(Continued)

(52) U.S. Cl.
CPC .............. *A61B 34/32* (2016.02); *A61B 34/20* (2016.02); *A61B 34/25* (2016.02); *A61B 34/30* (2016.02);
(Continued)

(58) Field of Classification Search
CPC ......... A61B 34/32; A61B 34/20; A61B 34/25; A61B 34/30; A61B 2034/2051; A61B 2034/2055; A61B 2034/2063; A61B 2090/3937; A61B 2090/5025; A61B 2090/508; A61B 90/50; B25J 9/1641; B25J 9/1643
USPC .............. 700/245; 248/123.11, 449; 73/1.79, 73/54.14, 854; 348/94, 154; 356/614; 702/166; 901/48
See application file for complete search history.

(56) References Cited

U.S. PATENT DOCUMENTS 4,132,937 A * 1/1979 Engelberger ......... G05B 19/318
5,024,087 A * 6/1991 Nagasaki ................ G01P 15/11
(Continued)

FOREIGN PATENT DOCUMENTS

CN     104736092 B1     7/2017
CN     105392438 B1     5/2018
(Continued)

OTHER PUBLICATIONS

International Search Report and Written Opinion for corresponding international application No. PCT/EP2019/075752, dated Jun. 26, 2020. 11 pages.

*Primary Examiner* — Ellis B. Ramirez
(74) *Attorney, Agent, or Firm* — Tucker Ellis LLP

(57)          ABSTRACT
The present application relates to a computer-implemented medical method of determining a compensation for gravity-related displacements of a medical carrier structure having at least one adjustable and selectively fixable joint which respectively connects two sections of the carrier structure. The present application further relates to a corresponding computer program and medical system.

20 Claims, 3 Drawing Sheets

(51) Int. Cl.
    *A61B 34/20*     (2016.01)
    *A61B 34/30*     (2016.01)
    *B25J 9/16*      (2006.01)

(52) U.S. Cl.
    CPC ..... B25J 9/1641 (2013.01); *A61B 2034/2051*
    (2016.02); *A61B 2034/2055* (2016.02); *A61B*
    *2034/2063* (2016.02)

(56)            References Cited

U.S. PATENT DOCUMENTS

| | | | |
|---|---|---|---|
| 5,234,282 A * | 8/1993 | Osborn | E01C 23/122 |
| 9,927,347 B1 * | 3/2018 | LoPresti | G01M 17/02 |
| 2002/0118793 A1 | 8/2002 | Horbaschek | |
| 2007/0080275 A1 * | 4/2007 | Stachowski | F16M 11/2014 |
| 2007/0151389 A1 * | 7/2007 | Prisco | B25J 9/1633 |
| 2008/0089467 A1 | 4/2008 | Gunter | |
| 2009/0180594 A1 | 7/2009 | Saladin | |
| 2010/0328683 A1 * | 12/2010 | Pan | G01B 11/06 |
| 2011/0162179 A1 * | 7/2011 | Howes | F01D 25/285 |
| 2013/0003927 A1 | 1/2013 | Tsujii | |
| 2013/0158386 A1 * | 6/2013 | Rotvold | A61B 34/20 |

| | | | |
|---|---|---|---|
| 2014/0039681 A1 | 2/2014 | Bowling et al. | |
| 2015/0105907 A1 * | 4/2015 | Aiso | B25J 9/1633 |
| 2016/0089211 A1 | 3/2016 | Bowling | |
| 2017/0027652 A1 * | 2/2017 | Johnson | A61B 90/50 |
| 2018/0194013 A1 | 7/2018 | Ruiz Morales et al. | |
| 2019/0176334 A1 | 6/2019 | Zhou et al. | |
| 2021/0059783 A1 * | 3/2021 | Haraguchi | A61B 1/00149 |
| 2021/0315652 A1 * | 10/2021 | Henrywood | A61B 34/74 |
| 2022/0110705 A1 * | 4/2022 | Hourtash | B25J 9/1689 |

FOREIGN PATENT DOCUMENTS

| | | | | |
|---|---|---|---|---|
| CN | 108289719 A1 | | 7/2018 | |
| CN | 108472028 A1 | | 8/2018 | |
| DE | 10 2012 102 294 B4 | | 11/2012 | |
| EP | 1 304 604 B1 | | 4/2003 | |
| EP | 1915963 A1 | | 4/2008 | |
| JP | 2016-519585 A1 | | 7/2016 | |
| KR | 20170047779 A | * | 5/2017 | |
| RU | 2518806 C2 | | 6/2014 | |
| WO | 2017/127202 A1 | | 7/2017 | |
| WO | 2018053349 A1 | | 3/2018 | |
| WO | 2019210322 A1 | | 10/2019 | |

* cited by examiner

COMPENSATION OF GRAVITY-RELATED DISPLACEMENTS OF MEDICAL CARRIER STRUCTURES

RELATED APPLICATION DATA

This application is a national phase application of International Application No. PCT/EP2020/066861, filed Jun. 18, 2020, the contents of which are incorporated herein by reference.

FIELD OF THE INVENTION

The present invention relates to a computer-implemented method of determining a compensation for gravity-related displacements of a medical carrier structure, a corresponding computer program, a computer-readable storage medium storing such a program and a computer executing the program, as well as a medical system comprising an electronic data storage device and the aforementioned computer.

TECHNICAL BACKGROUND

The usability of fully automatic or semi-automatic carrier structures such as robots for assisting in surgical procedures heavily depends on the grade of precision these carrier structures are able to provide in positioning and operating instruments and other medical appliances during the procedure. As such carrier structures are, as any mechanical construction, subject to tolerances and elastic deformations, that may result in undesired positional deviations as soon as gravity acts on these structures, measures have to be taken to work against these positional deviations.

Known robotic systems usually feature internal position sensors such as encoders disposed at the joints of the robot, which provide information as to the relative position of the robot's individual sections, ultimately allowing to calculate the robot's positional configuration within a three-dimensional space. This calculated position may however deviates from the actual spatial position by a certain amount because of the above reasons. Assuming that these deviations are repeatable for the same positional configuration, many prior art approaches rely on look-up-tables acquired from a prior system calibration, which indicates, for a sufficient number of positional configurations, the positional deviation to be expected. These additional information allows for compensating expected positional deviations when positioning the robot or carrier structure.

Actual positional deviations are however not considered by this prior art approach, which still leaves room for undetected positional inaccuracies. The present invention has the object to remedy this problem.

The present invention can be used for robot assisted surgical procedures e.g. in connection with a system such as Cirq®, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

The present invention relates to a computer-implemented medical method of determining a compensation for gravity-related displacements of a medical carrier structure having at least one adjustable and selectively fixable joint which respectively connects two sections of the carrier structure. The present invention further relates to a corresponding computer program and medical system.

GENERAL DESCRIPTION OF THE INVENTION

In general, the invention reaches the aforementioned object by providing, in a first aspect, a computer-implemented medical method of determining a compensation for gravity-related displacements of a medical carrier structure having at least one adjustable and selectively fixable joint which respectively connects two sections of the carrier structure, wherein the method comprises the following steps:

target position data is acquired which describes a target position for a predefined section of the carrier structure;

rest position data is acquired which describes a rest position into which the predefined section of the carrier structure is displaced by gravity after being positioned at the target position;

deviation data is determined based on the target position data and the rest position data, which describes a spatial deviation between the target position and the rest position;

prepositioning data is determined based on the deviation data, which describes an offset position at which the predefined section of the carrier structure needs to be positioned in order for it to be displaced by gravity into the target position.

In a (for example first) exemplary step, a target position for the predefined section, for example a distal and/or a functional section of the carrier structure, is defined, which enables the predefined section of the carrier structure to fulfil its intended purpose, for example holding a medical instrument at a desired position or guiding a medical instrument along a desired path or trajectory.

After the predefined section of the carrier structure has been moved to the desired target position, for example manually by medical personnel or, in case of a motorized carrier structure automatically by actuators, the positional configuration of the carrier structure maybe maintained by applying joint brakes, that immobilise/fix the joints connecting the sections of the carrier structure. With the brakes applied, the actuators can be put inoperative or an operator can let go of the carrier structure, whereupon the carrier structure may drop by a certain amount due to gravity and the above-mentioned mechanical tolerances and/or elastic deformations, until the brakes take full effect on holding the carrier structure. This results in a certain deviation of the position in which the predefined section of the carrier structure eventually comes to rest, from the position in which the predefined section was initially planned to be placed in.

In a (for example second) exemplary step, this rest position is determined, such that, in a (for example third) exemplary step, the deviation between this actual rest position and the intended target position can be calculated.

As the positional deviation is expected to be comparatively small as compared to the range of motion of the carrier structure, an intermediate or offset position can be calculated, in a (for example fourth) exemplary step, by "adding" the inverse amount of the determined deviation to the intended target position. Placing the predefined section in this intermediate position results in the predefined section deviating, by the determined amount and direction, into the desired target position.

In a specific embodiment of the present invention, the target position may be acquired in situ, for example via a tracking system, after the at least one joint is fixed, i.e. the corresponding brake(s) is/are applied, while the predefined section of the carrier structure is still held in the target position, for example by a practitioner grasping the predefined section or at least one actuator still being operative. In the alternative, the target position can be acquired from a predefined dataset which may describe a surgical plan.

In a further specific embodiment, the rest position data may be acquired, after the predefined section has come to rest at the rest position, via an external tracking system, particularly via the same tracking system that was used for acquiring the target position data.

In another specific embodiment, determining position data is further based on the rest position data, wherein the offset position is determined based on a spatial offset from the rest position, wherein the spatial offset is calculated from the spatial deviation between the target position and the rest position; or the target position data, wherein the offset position is determined based on a spatial offset from the target position, wherein the spatial offset is calculated from the spatial deviation between the target position and the rest position.

While, in the first case, the offset position can be calculated from basically adding, to the rest position, double the amount of the determined deviation opposite to the direction of the determined deviation, the second case relates to basically adding, to the initially defined target position, the amount of the determined deviation opposite to the direction of the determined deviation.

Both of these approaches may further take into account a virtual model of the carrier structure which may describe the positional configuration of the joints of the carrier structure. For example, the model may describe the spatial orientation of rotatable joints which helps in determining whether or not the current configuration of the carrier structure allows for compensating the determined deviation. In a specific example, if the rotational axes of all of the joints are oriented vertically, this current spatial configuration will not allow for compensating a vertical deviation of the predefined section.

Once the offset position has been determined, the inventive approach may continue with:

transmitting the prepositioning data to a graphical-user-interface-(GUI)-module adapted to output instructions to a user to manually position the predefined section at the offset position; and/or transmitting the prepositioning data to an actuator-control-module adapted to output control signals to at least one actuator to automatically position the predefined section at the offset position.

In other words, the determined offset position is processed to output instructions for a manual repositioning of the predefined section, or to output control signals for an automatic repositioning via one or more of the actuators, such that the predefined section can be repositioned in the offset position. For example, the actuators and/or the brakes are activated/released only for joints, particularly a minimum number of joints, which provide a degree of freedom required for the predefined section to reach the offset position, wherein the carrier structure is stabilized for the remaining degrees of freedom.

In a further specific embodiment, the target position data is acquired from a medical planning module on which a surgical plan is stored and/or processed. The target position may however as set out further above, also be determined in situ via a tracking system, i.e. when the predefined section is held in the desired target position.

Further, the rest position data may be acquired from a tracking system once the predefined section has come to rest in the rest position. This tracking system may either be an external tracking system or an internal tracking system of the carrier structure, wherein the latter may comprise position sensors assigned to the at least one joint.

One or more of the following tracking systems may be used to determine the target position and/or the rest position of the predefined section:

an optical tracking system;

an EM-tracking system;

an ultrasound tracking system;

a position sensor tracking system;

a capacitive tracking system;

a permanent magnetic tracking system.

While the position sensor tracking system may be considered as "internal" tracking system, the remaining systems may be considered as "external" tracking systems.

Further specific embodiments of the present invention can be configured as follows:

the carrier structure comprises a plurality of joints, wherein each one of the joints respectively connects two sections of the carrier structure;

at least one joint is a pivot joint providing a rotational degree of freedom;

at least one joint comprises a position sensor adapted to determine the relative position of the sections connected via the joint;

the predefined section is an end section of the carrier structure; and/or the carrier structure comprises a spatially invariant base section which connects to the predefined section via the at least one joint, particularly via at least one intermediate section.

In particular, the carrier structure may be represented by an articulated support arm which has a plurality of sequentially arranged arm sections connected to each other via rotatable joints. A first end section of the carrier structure may be a base section that takes a basically invariant spatial position. In this regard, spatially invariant means that the base section maintains its position within an operating theatre for at least a predefined period of time. For example, the base section may be disposed on a mobile cart or a similar appliance which maintains its spatial position within the operating theatre while a surgical procedure is carried out. In another example, the base section may be fixedly mounted to the floor or the ceiling of the operating theatre. Further, spatially invariant may also mean that the base section maintains its spatial position with respect to the patient on which the surgical procedure is carried out. For example, the base section may be fixedly attached to the mounting rail of a patient couch. In a still further example, the base section takes an invariant position by remaining stationary within a reference coordinate system in which the spatial position of the patient and medical appliances including further sections of the carrier structure is calculated.

At the other end of the carrier structure, which opposite to the base section, the carrier structure may comprise an end section which includes or which fixedly connects to functional components such as an effector for holding or guiding medical instruments or devices with respect to the patient's anatomy.

In a further embodiment of the present invention, the target position and the offset position assigned thereto are stored in a database, particularly wherein a plurality of target positions and assigned offset positions are stored in the database.

By doing so, the predefined section of the carrier structure can be (re-)positioned in an offset position which was previously determined for a desired target position, without the need of determining a rest position first. In other words, the predefined section of the carrier structure may be positioned in the offset position right away. The rest position and possible deviations from the target position may still be determined as a control measure, for example at predefined intervals, but need not be done every time when the predefined section is positioned. While this can be done for singular positions, for example when the predefined section needs to be repositioned at a target position which it was moved away from at an earlier point of time, storing a plurality of offset positions helps in mapping parts of or even the entire range of motion of the carrier structure, on which basis the predefined section may be positioned in a current or even in a future surgical procedure.

In future surgical procedures, a compensation for gravity-related displacements of the medical carrier structure may be retrieved from that database, particularly by performing the following steps:

acquiring target position data describing a target position for a predefined section of the carrier structure;

acquiring prepositioning data describing an offset position at which the predefined section of the carrier structure needs to be positioned in order for it to be displaced by gravity into the target position, wherein the prepositioning data is retrieved from a database storing at least one offset position, wherein the database is established by storing offset positions which were determined as described further above.

In case the predefined section is intended to be positioned in a target position for which no offset position is stored in the database, the offset position may, in a further embodiment of the present invention, be calculated on the basis of at least two offset positions assigned to target positions proximate to the unknown target position and stored in the database, particularly via an interpolation or an extrapolation.

According to a further embodiment of the present invention, offset positions determined for a plurality of medical carrier structures of the same type are stored in the database. By doing so, the data provided by the database is supplemented and updated in an efficient manner.

As was previously indicated, retrieving the offset position from a database and still determining the deviation between the rest position and the target position may not only serve for verification purposes, but may also help in detecting and evaluating wear and tear of the carrier structure over time, which is expected to result in an increased deviation between the target position and the rest position.

In a second aspect, the invention is directed to a computer program comprising instructions which, when the program is executed by at least one computer, causes the at least one computer to carry out method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. The signal wave is in one example a data carrier signal carrying the aforementioned computer program. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the second aspect therefore may alternatively or additionally relate to a data stream representative of the aforementioned program, i.e. comprising the program.

In a third aspect, the invention is directed to a computer-readable storage medium on which the program according to the second aspect is stored. The program storage medium is for example non-transitory.

In a fourth aspect, the invention is directed to at least one computer (for example, a computer), comprising at least one processor (for example, a processor), wherein the program according to the second aspect is executed by the processor, or wherein the at least one computer comprises the computer-readable storage medium according to the third aspect.

In a fifth aspect, the invention is directed to a medical system, comprising:

a) the at least one computer according to the fourth aspect;

b) at least one electronic data storage device storing at least the target position data; and c) a medical carrier structure having at least one adjustable and selectively fixable joint respectively connecting two sections of the medical carrier structure, wherein the at least one computer is operably coupled to the at least one electronic data storage device for acquiring, from the at least one data storage device, at least the target position data, and the medical carrier structure for issuing a control signal to the medical carrier structure for controlling the operation of the medical carrier structure on the basis of the target position data.

Alternatively or additionally, the invention according to the fifth aspect is directed to a for example non-transitory computer-readable program storage medium storing a program for causing the computer according to the fourth aspect to execute the data processing steps of the method according to the first aspect.

The invention does not involve or in particular comprise or encompass an invasive step which would represent a substantial physical interference with the body requiring professional medical expertise to be carried out and entailing a substantial health risk even when carried out with the required professional care and expertise.

DEFINITIONS

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a computer program comprising instructions which, when on the program is executed by a computer, cause the computer to carry out the method or methods, for example, the steps of the method or methods, described herein and/or to a computer-readable storage medium (for example, a non-transitory computer-readable storage medium) on which the program is stored and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein. The signal wave is in one example a data carrier signal carrying the aforementioned computer program. The invention also relates to a computer comprising at least one processor and/or the aforementioned computer-readable storage medium and for example a memory, wherein the program is executed by the processor.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows determining the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A "reference star" refers to a device with a number of markers, advantageously three markers, attached to it, wherein the markers are (for example detachably) attached to the reference star such that they are stationary, thus providing a known (and advantageously fixed) position of the markers relative to each other. The position of the markers relative to each other can be individually different for each reference star used within the framework of a surgical navigation method, in order to enable a surgical navigation system to identify the corresponding reference star on the basis of the position of its markers relative to each other. It is therefore also then possible for the objects (for example, instruments and/or parts of a body) to which the reference star is attached to be identified and/or differentiated accordingly. In a surgical navigation method, the reference star serves to attach a plurality of markers to an object (for example, a bone or a medical instrument) in order to be able to detect the position of the object (i.e. its spatial location and/or alignment). Such a reference star for example features a way of being attached to the object (for example, a clamp and/or a thread) and/or a holding element which ensures a distance between the markers and the object (for example in order to assist the visibility of the markers to a marker detection device) and/or marker holders which are mechanically connected to the holding element and which the markers can be attached to.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

The invention also relates to a navigation system for computer-assisted surgery, comprising:

a computer for processing the absolute point data and the relative point data;
    a detection device for detecting the position of the main and auxiliary points in order to generate the absolute point data and to supply the absolute point data to the computer;
    a data interface for receiving the relative point data and for supplying the relative point data to the computer; and
    a user interface for receiving data from the computer in order to provide information to the user, wherein the received data are generated by the computer on the basis of the results of the processing performed by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
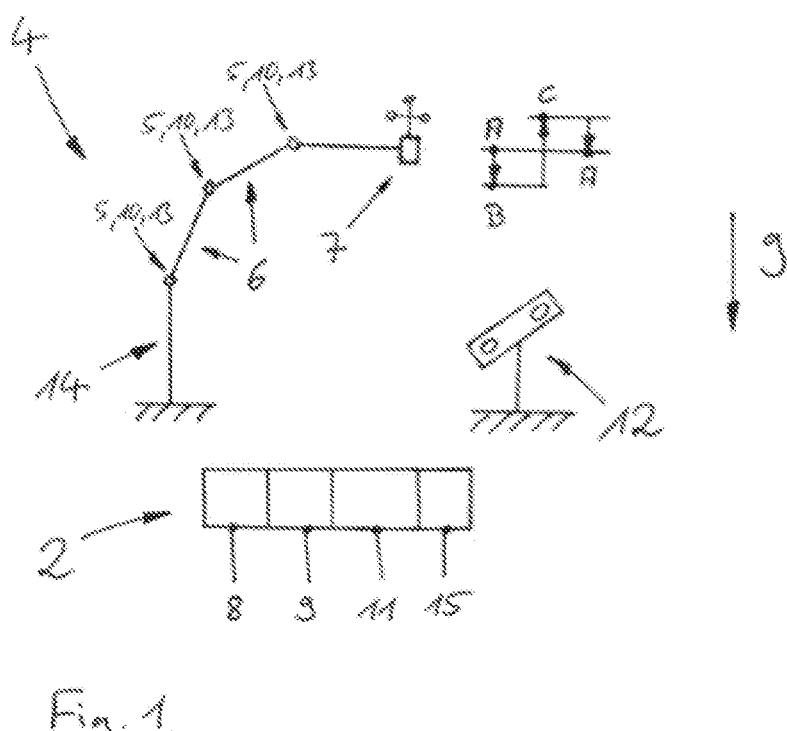
FIG. 1 shows a medical carrier structure, a computer and a navigation system as used in connection with the present invention.

FIG. 1 shows an articulated support arm 4 as used during robot assisted surgery, a distal, functional section 7 which is adapted to hold or guide medical instruments or devices with respect to a patient, and therefore comprises an effector. The distal, functional section 7 of the support arm 4 will be referred to in the following as "predefined section" 7. The support arm 4 further includes a base-section 14 which remains stationary with respect to the patient. The predefined section 7 is connected to the base section 14 via two intermediate sections 6, wherein the sections 6, 7, 14 are connected to each other via rotatable joints 5, each of which provides a single rotational degree of freedom. As the rotational axes of the joints are not arranged in parallel, the support arm 4 is adapted to hold the predefined section 7 at any desired spatial position.

Further, the joints 5 do not only comprise a position sensor 13 adapted to sense the angle between the arm sections 6, 7, 14 connected via the corresponding joint 5, but also comprise means, for example joint brakes, to immobilize the corresponding joints 5, i.e. to fix the relative position of the adjacent arm sections 6, 7, 14. Optionally, some or all of the joints 5 may also comprise actuators 10, for example servo motors, which are adapted to change the relative angular arrangement of the corresponding arm sections 6, 7, 14, so as to position the predefined section 7 in a desired position fully automatically. In the alternative, the support arm 4 may be operated manually, wherein the predefined section 7 is grasped and moved to the desired position by a practitioner, who may, while doing so, receive assisting guidance information, e.g. on a graphical user interface of the navigation system, indicating the necessary positional adjustments so as to have the predefined section 7 positioned at the desired position.

Assuming that the distal tip (end effector) of a predefined section 7 needs to be placed at a target position A (represented by height A in FIG. 1) in order to fulfil a desired purpose, merely positioning the distal tip at position A and applying the joint brakes will most likely be followed by a vertical displacement of the distal tip into position B (represented by height B), which is caused not only by an inherent play within the joint breaks, but also by the elastic properties inherent to each one of the arm sections 6, 7, 14. The amount and direction by which the distal tip of the predefined section 7 will deflect, i.e. the deviation of position B with respect to position A depends on the direction of the gravity-vector g with respect to the support arm 4, the load attached to the support arm 4, the tare weight of the support arm 4, and the spatial configuration of the support arm 4, i.e. the current spatial orientation of the rotatable joints 5 and the current horizontal overhang of the predefined section's 7 distal tip with respect to the mounting of the base section 14 to a solid foundation.

In order to compensate for this deviation, the spatial deviation of position B from position A is determined, which is for the shown example substantially vertical. Thus, adding double the amount of the determined downward displacement to height B in an upward direction leads to an offset position C (represented by height C) which is the position/ height from which the distal tip of the predefined section 7 will deflect into the desired target position A.

In order to determine the rest position B, the distal tip of the predefined section 7 is provided with a marker array adapted to be recognised by an optical navigation system 12 that includes a stereo-camera-array.

Once the offset position C has been determined in accordance with the present invention, the distal tip of the predefined section 7 can be positioned there, either automatically by controlling the actuators 10 and the joint brakes in the affected joints, or by instructing a practitioner, for example via a graphical-user-interface. For positioning the distal tip of the predefined section 7 in the offset position C, only those joints 5 are unlocked by releasing the corresponding brakes, which are necessary for the predefined section 7 to reach the offset position C. The remaining joints 5 remain locked, thereby providing guidance for repositioning the predefined section 7.

In case the current spatial arrangement of the joints 5 does not allow for such repositioning (in the shown example, this may be the case with each one of the rotatable joints 5 having a vertical axis of rotation), the rotational axis of one or more selected joint(s) 5 may be reoriented so as to allow the desired repositioning, for example by activating one or more of the remaining joint actuators 10, or by outputting corresponding instructions to the practitioner.

FIG. 1 further schematically shows a graphical-user-interface-(GUI)-module 8 adapted to output instructions to a user/practitioner, an actuator-control-module 9 adapted to output control signals to at least one actuator 10, a medical planning module which stores a treatment plan that may include position A as a desired target position, and a database 15 the offset position C assigned to the target position A can be stored on and/or retrieved from. All of these components are comprised within a computer 2 connected to the medical support arm 4 and the tracking system 12.

Figure 2:
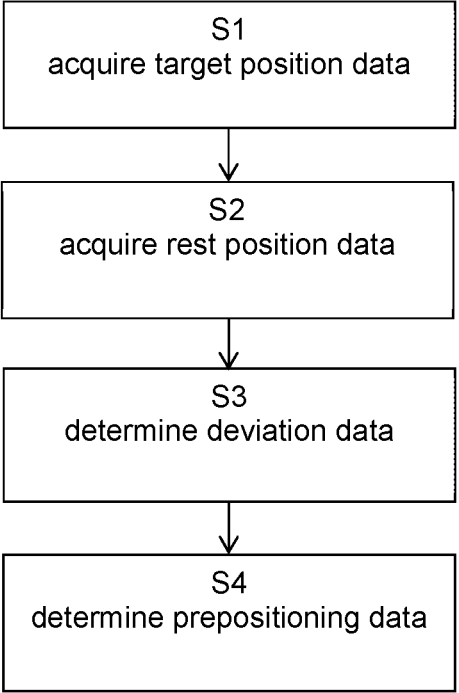
FIG. 2 shows the basic steps of the method according to the first aspect.

FIG. 2 shows the basic steps of the method according to the present invention. As a first step S1, data describing the target position A for the predefined section 7 is acquired. After the predefined section 7 has come to rest after having been placed in the target position A, data describing this rest position B is acquired. In a third step S3, the spatial deviation between these positions is determined and, in a fourth step S4, an offset position C is calculated based on the determined spatial deviation.

Figure 3:
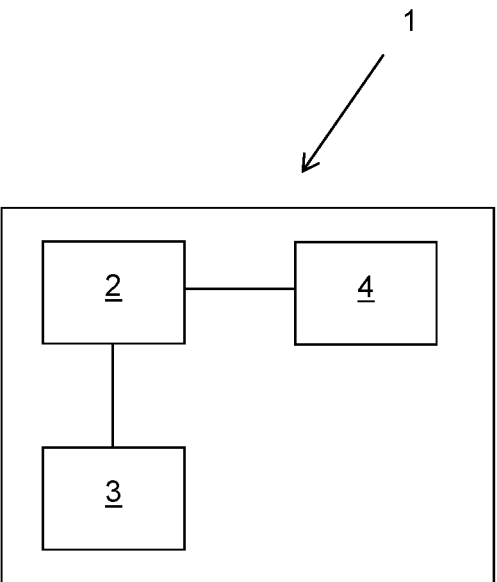
FIG. 3 is a schematic illustration of the system according to the fifth aspect.

FIG. 3 is a schematic illustration of the medical system 1 according to the fifth aspect. The system comprises at least one computer 2, at least one data storage device 3 for retrieving at least the target position data, and the medical carrier structure 4 as shown in FIG. 1. The components of the medical system 1 have the functionalities and properties explained above with regard to the fifth aspect of this disclosure.

The invention claimed is:

1. A computer-implemented method of determining a compensation for gravity-related displacements of a medical carrier structure having at least one adjustable joint including a joint brake to selectively immobilize the joint which respectively connects two sections of the medical carrier structure, the method comprising:

acquiring target position data which describes a target position for a predefined section of the medical carrier structure, the target position being a position at which the predefined section is intended to be held by a positional configuration of the medical carrier structure;

acquiring rest position data which describes a rest position into which the predefined section of the medical carrier structure is displaced by gravity, wherein the acquiring the rest position data comprises:

positioning the predefined section of the medical carrier structure at the target position;

applying the brake to immobilize the at least one joint; and allowing the predefined section of the medical carrier structure to deviate from the target position into the rest position due to gravity and without any actuator effects or support from an operator;

determining deviation data based on the target position data and the rest position data, wherein the deviation data describes a spatial deviation between the target position and the rest position; and determining prepositioning data based on the deviation data, wherein the prepositioning data describes an offset position at which the predefined section of the medical carrier structure needs to be positioned, the offset position being representative of an amount and direction of deviation of the predefined section, in order for the predefined section of the medical carrier structure to be displaced by gravity into the target position at which the predefined section is intended to be held in place by the positional configuration of the medical carrier structure.

2. The method according to claim 1, wherein the acquiring target position data comprises acquiring target position data after the at least one joint is immobilized, with the predefined section of the medical carrier structure being held at the target position.

3. The method according to claim 1, wherein the acquiring rest position data comprises acquiring rest position data after the predefined section has come to rest at the rest position.

4. The method according to claim 1, wherein determining prepositioning data is further based on:

the rest position data, wherein the offset position is determined based on a spatial offset from the rest position, wherein the spatial offset is calculated from the spatial deviation between the target position and the rest position; or the target position data, wherein the offset position is determined based on a spatial offset from the target position, wherein the spatial offset is calculated from the spatial deviation between the target position and the rest position.

5. The method according to claim 1, further comprising:

transmitting the prepositioning data to a graphical-user-interface-(GUI)-module adapted to output instructions to a user to manually position the predefined section at the offset position; and/or transmitting the prepositioning data to an actuator-control-module adapted to output control signals to at least one actuator to automatically position the predefined section at the offset position.

6. The method according to claim 1, wherein the acquiring target position data comprises acquiring target position data from a medical planning module and/or from at least one tracking system adapted to determine a spatial position of the predefined section.

7. The method according to claim 1, wherein the acquiring rest position data comprises acquiring rest position data from at least one tracking system adapted to determine a spatial position of the predefined section.

8. The method according to claim 6, wherein the target position data is acquired from the at least one tracking system, wherein the at least one tracking system is selected from the group consisting of:

an optical tracking system;
an EM-tracking system;
an ultrasound tracking system;
a position sensor tracking system;
a capacitive tracking system; and
a permanent magnetic tracking system.

9. The method according to claim 1, wherein:

the medical carrier structure comprises a plurality of joints, and wherein each one of the joints respectively connects two sections of the medical carrier structure;

at least one joint is a pivot joint providing a rotational degree of freedom;

at least one joint comprises a position sensor adapted to determine a relative position of the sections connected via the joint;

the predefined section is an end section of the medical carrier structure; and/or the medical carrier structure comprises a spatially invariant base section which connects to the predefined section via the at least one joint.

10. The method according to claim 1, further comprising:

storing the target position and an assigned offset position in a database.

11. The method according to claim 10, further comprising:

acquiring target position data describing the target position for the predefined section of the medical carrier structure; and acquiring, from the database storing at least one offset position, prepositioning data describing the offset position at which the predefined section of the medical carrier structure needs to be positioned in order for the predefined section of the medical carrier structure to be displaced by gravity into the target position with the at least one joint being immobilized and the predefined section of the medical carrier structure being free of any actuator effects or support from an operator.

12. The method according to claim 11, further comprising:

calculating an offset position assigned to a new target position based on at least two offset positions assigned to target positions stored in the database and proximate to an unknown target position.

13. The method according to claim 11, wherein offset positions determined for a plurality of medical carrier structures are stored in the database.

14. A non-transitory computer readable storage medium storing a program comprising program instructions, that when executed on at least one processor of a computer or loaded onto the at least one processor of the computer, causes the computer to perform a method of determining a compensation for gravity-related displacements of a medical carrier structure having at least one adjustable joint including a joint brake to selectively immobilize the joint which respectively connects two sections of the medical carrier structure by:

acquiring target position data which describes a target position for a predefined section of the medical carrier structure, the target position being a position at which the predefined section is intended to be held by a positional configuration of the medical carrier structure;

acquiring rest position data which describes a rest position into which the predefined section of the medical carrier structure is displaced by gravity, wherein the acquiring the rest position data comprises:

positioning the predefined section of the medical carrier structure at the target position;

applying the brake to immobilize the at least one joint; and allowing the predefined section of the medical carrier structure to deviate from the target position into the rest position due to gravity and without any actuator effects or support from an operator;

determining deviation data based on the target position data and the rest position data, wherein the deviation data describes a spatial deviation between the target position and the rest position; and determining prepositioning data based on the deviation data, wherein the prepositioning data describes an offset position at which the predefined section of the medical carrier structure needs to be positioned, the offset position being representative of an amount and direction of deviation of the predefined section, in order for the predefined section of the medical carrier structure to be displaced by gravity into the target position at which the predefined section is intended to be held in place by the positional configuration of the medical carrier structure.

15. A medical system, comprising:

at least one computer;

at least one electronic data storage device storing at least target position data; and a medical carrier structure having at least one adjustable joint including a joint brake to selectively immobilize the joint respectively connecting two sections of the medical carrier structure, wherein the at least one computer is operable to:

acquire, from the at least one electronic data storage device, the target position data, wherein the target position data describes a target position for a predefined section of the medical carrier structure having the at least one joint which respectively connects two sections of the medical carrier structure, the target position being a position at which the predefined section is intended to be held by a positional configuration of the medical carrier structure;

acquire rest position data which describes a rest position into which the predefined section of the medical carrier structure is displaced by gravity, wherein the acquiring the rest position data comprises:

positioning the predefined section of the medical carrier structure at the target position;

applying the brake to immobilize the at least one joint; and allowing the predefined section of the medical carrier structure to deviate from the target position into the rest position due to gravity and without any actuator effects or support from an operator;

determine deviation data based on the target position data and the rest position data, wherein the deviation data describes a spatial deviation between the target position and the rest position;

determine prepositioning data based on the deviation data, wherein the prepositioning data describes an offset position at which the predefined section of the medical carrier structure needs to be positioned, the offset position being representative of an amount and direction of deviation of the predefined section, in order for the predefined section of the medical carrier structure to be displaced by gravity into the target position at which the predefined section is intended to be held in place by the positional configuration of the medical carrier structure; and issue a control signal to the medical carrier structure for controlling operation of the medical carrier structure based on the target position data.

16. The method according to claim 10, wherein a plurality of target positions and the assigned offset positions are stored in the database.

17. The method according to claim 12, wherein the calculating the offset position comprises calculating the offset position assigned to the new target position via interpolation or extrapolation.

18. The method according to claim 1, wherein:

the allowing the predefined section of the medical carrier structure to deviate from the target position into the rest position comprises:

allowing the predefined section of the medical carrier structure to deviate from the target position into the rest position after the applying the brake to immobilize the at least one joint; and the applying the brake to immobilize the at least one joint comprises:

applying the brake to immobilize the at least one joint after positioning the predefined section of the medical carrier structure at the target position.

19. The non-transitory computer readable storage medium storing the program comprising program instructions according to claim 14, wherein when the program instructions are executed on the at least one processor of the computer or loaded onto the at least one processor of the computer, cause the computer to:

allow the predefined section of the medical carrier structure to deviate from the target position into the rest position by:

allowing the predefined section of the medical carrier structure to deviate from the target position into the rest position after the applying the brake to immobilize the at least one joint; and apply the brake to immobilize the at least one joint by:

applying the brake to immobilize the at least one joint after positioning the predefined section of the medical carrier structure at the target position.

20. The medical system according to claim 15, wherein the at least one computer is operable to:

allow the predefined section of the medical carrier structure to deviate from the target position into the rest position by:

allowing the predefined section of the medical carrier structure to deviate from the target position into the rest position after the applying the brake to immobilize the at least one joint; and apply the brake to immobilize the at least one joint by:

applying the brake to immobilize the at least one joint after positioning the predefined section of the medical carrier structure at the target position.

* * * * *